(12) United States Patent
Kawada et al.

(10) Patent No.: US 8,129,543 B2
(45) Date of Patent: Mar. 6, 2012

(54) CYCLIC GUANIDINE IONIC LIQUID

(75) Inventors: Atsushi Kawada, Kitakyushu (JP); Aya Tashiro, Kitakyushu (JP); Toshihiro Kumagai, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 98 days.

(21) Appl. No.: 12/529,590

(22) PCT Filed: Feb. 26, 2008

(86) PCT No.: PCT/JP2008/053295
§ 371 (c)(1),
(2), (4) Date: Sep. 2, 2009

(87) PCT Pub. No.: WO2008/108221
PCT Pub. Date: Sep. 12, 2008

(65) Prior Publication Data
US 2010/0121074 A1      May 13, 2010

(30) Foreign Application Priority Data
Mar. 6, 2007   (JP) .................................. 2007-055629

(51) Int. Cl.
*C07D 403/02* (2006.01)
(52) U.S. Cl. .................................................. 548/314.7
(58) Field of Classification Search .......................... None
See application file for complete search history.

(56) References Cited

U.S. PATENT DOCUMENTS

2007/0142642 A1   6/2007   Szarvas et al.
2008/0027230 A1   1/2008   Ignatyev et al.

FOREIGN PATENT DOCUMENTS

| | | |
|---|---|---|
| JP | 2004-253357 A | 9/2004 |
| WO | WO-2005/085207 A2 | 9/2005 |
| WO | WO-2006/007912 A1 | 1/2006 |

OTHER PUBLICATIONS

Dubey et al., caplus an 1978:509247.*
International Search Report for the Application No. PCT/JP2008/053295 mailed May 20, 2008.
International Preliminary Report on Patentability for Application No. PCT/JP2008/053295 mailed Sep. 17, 2009.
Gao, Haixiang et al., "Preparation of Room-Temperature Ionic Liquids by Neutralization of 1,1,3,3-Tetramethylguanidine with Acids and Their Use as Media for Mannich Reaction", Synthetic Communications, 2004, vol. 34, No. 17, pp. 3083-3089.
Wang, P. et al., "Novel Room Temperature Ionic Liquids of Hexaalkyl Substituted Guanidinium Salts for Dye-Sensitized Solar Cells", Applied Physics A, 2004, vol. 79, pp. 73-77.

* cited by examiner

*Primary Examiner* — Sun Jae Loewe
(74) *Attorney, Agent, or Firm* — Cheng Law Group, PLLC

(57) ABSTRACT

Disclosed is an ionic liquid which is stable over a wide potential range and exhibits a high ionic conductivity. The ionic liquid comprises a cyclic guanidine salt represented by the following formula (1):

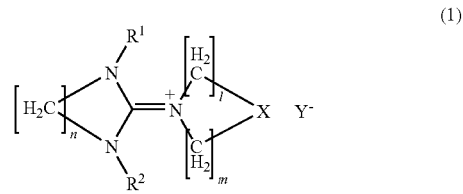

(1)

wherein $R^1$ and $R^2$ each is independently an alkyl group or an alkoxyalkyl group, X is a methylene group, an oxygen atom, a sulfur atom, or $R^3N$; $R^3$ is an alkyl group, an alkoxyalkyl group, or an acyl group; l, m, and n each is an integer in the range of 1-6; $Y^-$ is a monovalent anion such as $(R^4SO_2)_2N^-$, $R^4SO_3^-$, $R^4COO^-$, $BF_4^-$, $PF_6^-$, $NO_3^-$, $(CN)_2N^-$, $(CHO)_2N^-$, $NCS^-$, $R^4OSO_3^-$, $R^4SO_2S^-$, and a halogen ion. The ionic liquid is useful for a variety of electrolytes, particularly for electrolytes of electrochemical cells.

9 Claims, No Drawings

CYCLIC GUANIDINE IONIC LIQUID

TECHNICAL FIELD

This invention relates to a novel ionic liquid containing a cyclic guanidine cation useful as an electrolyte for electrochemical devices.

BACKGROUND TECHNOLOGY

Solutions of electrolytes in organic solvents such as propylene carbonate, γ-butyrolactone, and acetonitrile have been used as nonaqueous electrolytes for electrochemical devices such as lithium batteries, electric double-layer capacitors, electrochromic devices, and dye-sensitized solar cells. However, organic solvents used for these electrolyte solutions volatilize easily and besides they themselves are hazardous materials; therefore, concern has been expressed over their reliability, durability, and safety over a long period of time.

One of the methods to solve the aforementioned problems is to use an ionic liquid for an electrolyte. The term "ionic liquid" is commonly used for a compound which consists of a combination of anions and cations and has a melting point of 100° C. or below and it is reported in the non-patent document 1 that a combination of ions to suit the purpose can display required characteristics.

Several proposals have been made on electrolytes useful for electrochemical devices. For example, alkyl-substituted imidazolium salts are described in the patent documents 1-4 and quaternary alkylammonium salts in the patent documents 5-8.

In spite of the aforementioned report on the possibility that a combination of ions to suit the purpose can display required characteristics, what are actually used in most of current developmental works are quaternary imidazolium salts, alicyclic quaternary ammonium salts, quaternary alkylammonium salts, and the like and it has been considered necessary to develop materials of a novel skeleton for a breakthrough.

The inventors of this invention have searched for a novel skeleton aiming at developing electrolytes useful for electrochemical devices and devoted attention to a singularity in the chemical structure of guanidine compounds, namely, the structure of nonlocalized electrons. Guanidine compounds have hitherto been used as raw materials for pharmaceuticals, dyes, paints, photographic chemicals, and additives for polymers. Regarding the electrochemical properties of guanidine compounds, reports on the Bronsted acid salts of acyclic tetramethylguanidine are known (patent document 9 and non-patent document 2), but the salts are limited to protonic compounds. Regarding quaternary guanidine compounds, a compound having a hexaalkylguanidine cation is reported (non-patent document 2), but an account in the report is limited to applications of acyclic quaternary guanidine compounds to dye-sensitized solar cells.

Patent document 1: JP8-259543 A
Patent document 2: JP2003-62467 A
Patent document 3: JPH11-86905 A
Patent document 4: JP347213 C
Patent document 5: WO02/076924 A
Patent document 6: JP2003-331918 A
Patent document 7: JP2981545 C
Patent document 8: JP2004-67543 A
Patent document 9: JP2004-253357 A
Non-patent document 1: Chem. & Eng. News, May 15, 2000
Non-patent document 2: Synthetic Communication, Vol. 34, pp. 3083-3089 (2004)
Non-patent document 3: Appl. Phys. A, 79, 73-77 (2004)

DISCLOSURE OF THE INVENTION

Problems to be Solved by the Invention

An object of this invention is to provide an ionic liquid which is stable over a wide potential range and exhibits a high ionic conductivity.

Means to Solve the Problems

The inventors have conducted extensive researches to solve the aforementioned problems, found that an ionic liquid containing a cation derived from a cyclic guanidine is stable over a wide potential range and exhibits a high ionic conductivity, and arrived at this invention.

This invention relates to an ionic liquid comprising a cyclic guanidine salt represented by the following formula (1);

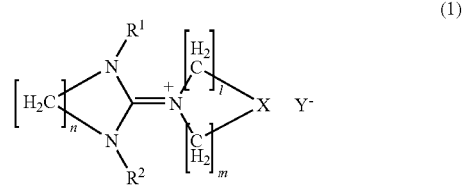

(1)

wherein $R^1$ and $R^2$ each is an alkyl group or an alkoxyalkyl group and X is a methylene group, an oxygen atom, a sulfur atom, or $R^3N$; $R^3$ is an alkyl group, an alkoxyalkyl group, or an acyl group; l, m, and n each is independently an integer of 1-6; and $Y^-$ is a monovalent anion.

In formula (1), $Y^-$ is selected preferably from the group of $(R^4SO_2)_2N^-$, $R^4SO_3^-$, $R^4COO^-$, $BF_4^-$, $PF_6^-$, $NO_3^-$, $(CN)_2N^-$, $(CHO)_2N^-$, $NCS^-$, $R^4OSO_3^-$, $R^4SO_2S^-$, and halogen ions. In $(R^4SO_2)_2N^-$, $R^4SO_3^-$, $R^4COO^-$, $R^4OSO_3^-$, and $R^4SO_2S^-$, $R^4$ is a perfluoroalkyl group, an alkyl group, or an aromatic group.

Further, this invention relates to a method for producing an ionic liquid represented by formula (1) by the reaction of a cyclic urea represented by formula (2) with a compound represented by formula (3):

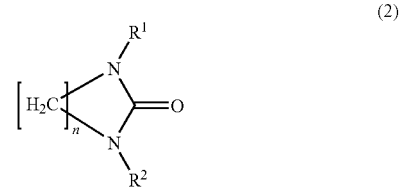

(2)

wherein, $R^1$, $R^2$ and n have the same meaning as in formula (1).

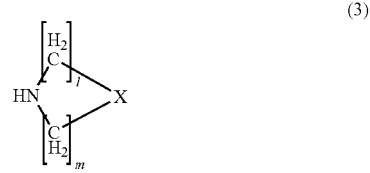

(3)

wherein, X, l, and n have the same meaning as in formula (1).

The reaction of a cyclic urea represented by formula (2) with a compound represented by formula (3) is accelerated either by allowing a reaction accelerator to exist with the reactants or by reacting a cyclic urea represented by formula (2) first with a reaction accelerator and then with a compound represented by formula (3).

Further, this invention relates to an electrolyte containing an ionic liquid represented by formula (1) and, still further, this invention relates to an electrochemical cell using an electrolyte containing said ionic liquid.

PREFERRED EMBODIMENTS OF THE INVENTION

An ionic liquid according to this invention comprises a cyclic guanidine salt represented by the aforementioned formula (1) and said ionic liquid itself is also represented by formula (1). In the formula, $R^1$ and $R^2$ each is an alkyl group or an alkoxyalkyl group and $R^1$ may be identical with or different from $R^2$. Preferable examples of the alkyl group include alkyl groups of 1-12 carbon atoms. Preferable examples of the alkoxyalkyl group include lower alkoxyalkyl groups of 1-8 carbon atoms; for example, a methoxymethyl group, a methoxyethyl group, a methoxypropyl group, an ethoxyethyl group, an ethoxypropyl group, an ethoxybutyl group, a propyloxyethyl group, an isopropyloxyethyl group, an isopropyloxypropyl group, a butoxyethyl group, a butoxypropyl group, and a butoxybutyl group.

The group X is a methylene group, an alkoxyalkylamino group, an oxygen atom, a sulfur atom, or $R^3N$; $R^3$ is an alkyl group, an alkoxyalkyl group, or an acyl group. In the case where $R^3$ is an alkyl group or an alkoxyalkyl group, the alkyl or alkoxyalkyl group is preferably the same as those cited above. In the case where X is an alkoxyalkylamino group, the alkoxyalkyl moiety is preferably the same as those cited above. An acyl group of 1-8 carbon atoms is preferable where $R^3$ is an acyl group; for example, an acetyl group, an ethylcarbonyl group, and a benzoyl group.

The numbers l, m, and n each is independently an integer of 1-6 and, preferably, l and m each is an integer of 1-3 and n is 2 or 3.

The group $Y^-$ is a monovalent anion and selected preferably from $(R^4SO_2)_2N^-$, $R^4SO_3^-$, $R^4COO^-$, $BF_4^-$, $PF_6^-$, $NO_3^-$, $(CN)_2N^-$, $(CHO)_2N^-$, $NCS^-$, $R^4OSO_3^-$, $R^4SO_2S^-$, and halogen ions. Here, $R^4$ is a perfluoroalkyl group, an alkyl group, or an aromatic group. Perfluoroalkyl groups of 1-8 carbon atoms or alkyl groups of 1-12 carbon atoms are preferred. The aromatic group may be substituted or unsubstituted and an unsubstituted or substituted phenyl group is preferred. Examples of such phenyl groups include a phenyl group, alkylphenyl groups, alkyloxyphenyl groups, halogenated phenyl groups, nitrophenyl groups, acylphenyl groups, and alkoxycarbonylphenyl groups.

Although a cyclic guanidine salt represented by formula (1) can be prepared by a known method, it can be prepared efficiently according to the reaction shown below.

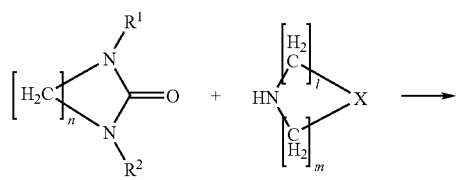

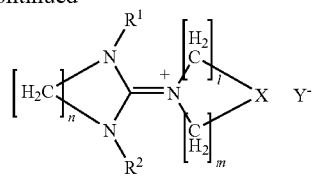

This method is based on the reaction of a cyclic urea compound represented by formula (2) with a compound represented by formula (3) and $R^1$, $R^2$, and n in formula (2) and X, l, and m in formula (3) have the same meaning as in formula (1).

In the aforementioned method using a cyclic urea compound represented by formula (2) and a compound represented by formula (3), it is preferable to introduce a leaving group to the carbon atom of the carbonyl group in a cyclic urea compound represented by formula (2) by means of a reaction accelerator in order to enhance the reactivity of the cyclic urea compound and then to allow a leaving group-containing cyclic urea derivative to react with a compound represented by formula (3). A halogen such as chlorine and bromine is preferably used as a leaving group. For example, this procedure is carried out as follows: a chlorinating agent as a reaction accelerator is allowed to react with a cyclic urea compound represented by formula (2) to chlorinate the carbonyl carbon of the cyclic urea compound thereby yielding a chlorinated derivative of the cyclic urea compound and said derivative is then submitted to the reaction with a compound represented by formula (3). This chlorination reaction is usually carried out in a solvent in the presence of the chlorinating agent. The chlorinating agents useful for the reaction include phosphorus oxychloride, phosgene, and thionyl chloride. The chlorinating agent is normally used in an amount more than is theoretically required for the reaction with a cyclic urea compound represented by formula (2). On the other hand, consideration of difficulty or ease of availability of cyclic urea compounds and of removal of byproducts formed by the chlorinating agent in the reaction may sometimes economically favors the use of less chlorinating agent than is theoretically required on a molar basis. The aforementioned chlorinated product is assumed to be a compound shown by the following formula.

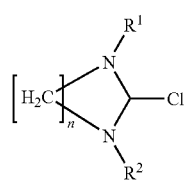

The aforementioned chlorination reaction is carried out advantageously in a solvent. Any solvent which does not interfere with the reaction may be used and preferable examples include aliphatic hydrocarbons such as hexane, heptane, and petroleum ether, aromatic hydrocarbons such as benzene, toluene, and xylene, organic nitro compounds such as nitromethane and nitrobenzene, cyclic ethers such as tetrahydrofuran and dioxane, and halogen-containing compounds such as dichloromethane, chloroform, and tetrachloroethane. The reaction temperature for the chlorination reaction usually ranges from room temperature to 150° C., preferably from 50 to 100° C. The reaction time is usually in the range of 0.5-24 hours, preferably in the range of 1-10 hours.

In the case where a cyclic urea compound represented by formula (2) is chlorinated first and the reaction mixture is then made to react with a compound represented by formula (3), it is optional either to isolate the chlorinated product from the reaction mixture or to add a compound represented by formula (3) to the reaction mixture. After the chlorination reaction is over, there may arise a case where the chlorinated product does not dissolve in the reaction solvent and precipitates out or undergoes phase separation. In such a case, a solvent is newly added to dissolve the chlorinated product. The same solvent as used in the chlorination reaction can be used here. A compound represented by formula (3) is added at a rate of 1 mole or more, preferably 1-2.5 moles, to 1 mole of a chlorinating agent. In order to advance the reaction of the chlorinated product with the compound represented by formula (3) smoothly, it is allowable to use a base catalyst. The useful base catalysts include tertiary alkylamines such as triethylamine, tertiary alicyclic amines such as N-methylpyrrolidone, and aromatic amines such as pyridine and quinoline. The reaction temperature is normally in the range of room temperature to 100° C., preferably in the range of 30-70° C. The reaction time is normally in the range of 0.5-24 hours, preferably in the range of 1-10 hours.

Upon completion of the reaction, the reaction mixture is treated in the usual manner to give a cyclic guanidine salt represented by formula (1). The anion $Y^-$ can be obtained as desired according to the treating method used and, preferably, a variety of cyclic guanidine salts differing in $Y^-$ can be obtained as follows. After the chlorination of a cyclic urea represented by formula (2) is over, the chlorinated product is made to react with a compound represented by formula (3), the reaction mixture is treated with an adsorbent such as silica gel to remove the byproducts and unchanged raw materials, and the solvent is distilled off to give a cyclic guanidine salt having $Cl^-$ as an anion. If necessary, said cyclic guanidine salt is submitted to salt exchange reaction, which can be carried out as in the salt exchange reactions known for quaternary ammonium salts and the like.

Examples of the cationic moieties (cyclic guanidine salt less $Y^-$) of the cyclic guanidine salts represented by formula (1) are shown below, but the cations useful for this invention are not limited to these examples. A number is assigned to each cation beneath its chemical formula. Preferable cyclic guanidine salts comprise the cations listed here and the anions represented by $Y^-$.

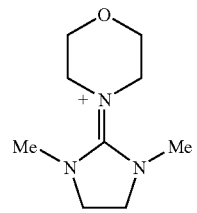

1

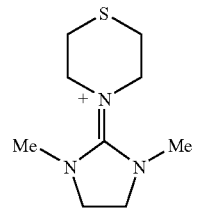

2

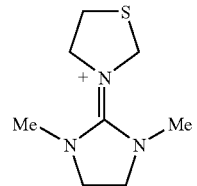

3

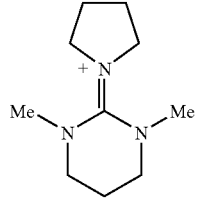

4

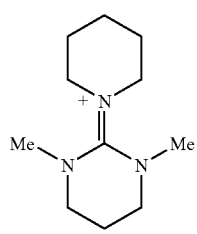

5

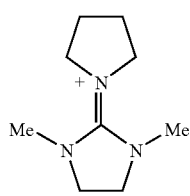

6

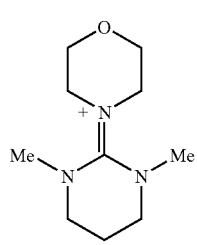

7

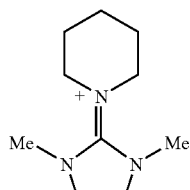

8

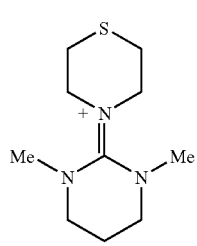

9

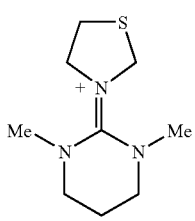

10

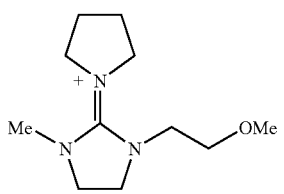

11

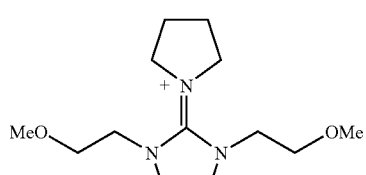

12

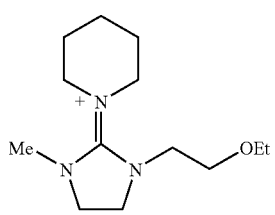

13

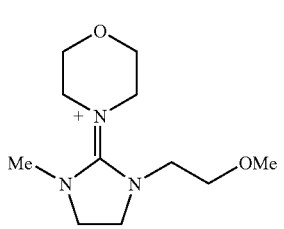

14

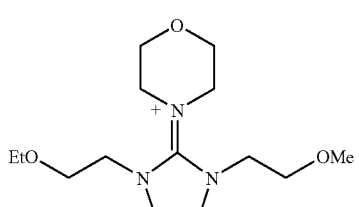

15

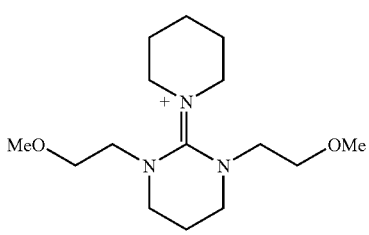

16

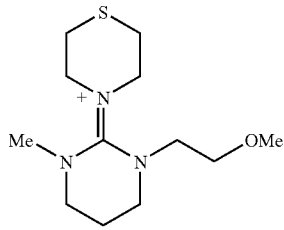

17

A cyclic guanidine salt represented by formula (1) generally has a low melting point and exhibits a high ionic conductivity; hence, it can be used as an electrolyte for a variety of electrochemical devices such as lithium ion primary batteries, lithium ion secondary batteries, dye-sensitized solar cells, electric double layer capacitors, and electrochromic devices. When an ionic liquid represented by formula (1) according to this invention is used in the aforementioned applications, it is optional either to use a single kind or to use a mixture of two kinds or more. When an ionic liquid of this invention is used in an application requiring an ionic liquid, it is allowable for said ionic liquid to contain other components which do not harm the function of said ionic liquid. For example, when it is used as an electrolyte in an electrochemical device, a cyclic guanidine salt represented by formula (1) may be mixed with another salt which can be used as an electrolyte in said electrochemical device. Moreover, a cyclic guanidine salt represented by formula (1) or its mixture with another salt may be used dissolved in a solvent.

EXAMPLES

This invention will be described in more detail below with reference to the examples.

Example 1

In a three-necked flask equipped with a dropping funnel and a reflux condenser were placed 19.4 g (170 millimoles) of 1,3-dimethyl-2-imidazolidinone and 50 mL of toluene in an atmosphere of nitrogen. Then, 13.0 g (85 millimoles) of phosphorus oxychloride was added and stirred at 65° C. Heating was stopped after 1 hour, the flask was cooled in an ice bath, and a solution containing the chlorination product of 1,3-dimethyl-2-imidazolidinone was obtained. To this solution were added 50 mL of dichloromethane and 23.6 mL (170 millimoles) of triethylamine in succession. To the resulting solution was added dropwise a solution of 13.8 mL (170 millimoles) of pyrrolidine in 50 mL of dichloromethane over a period of approximately 30 minutes while cooling the solution in an ice bath. Upon completion of the dropwise addition, the ice bath was removed and the solution was stirred at 55° C. The reaction mixture was cooled to room temperature after 1 hour, the insoluble matters were removed by filtration, and the filtrate was distilled off under reduced pressure. The residue was purified by column chromatography to give 15.9 g of 4,5-dihydro-1,3-dimethyl-2-(1-pyrrolidinyl)-1H-imidazolium chloride as a light yellow solid; this compound is a cyclic guanidine salt comprising the cation designated by chemical formula I and Cl− and is hereinafter referred to as cyclic guanidine salt 1. The solid showed a melting point of 49° C. and was hence a cyclic guanidine salt qualified for an ionic liquid.

In 100 mL of dichloromethane was dissolved 5.08 g (24.9 millimoles) of cyclic guanidine salt 1 obtained above. To this solution was added 7.30 g (25.4 millimoles) of lithium bis(trifluoromethanesulfonyl)imide and the mixture was stirred at room temperature for 1 hour. The white precipitate formed was filtered off and the filtrate was washed with deionized water and concentrated in a rotary evaporator. The residue was dissolved in methanol and the solution was stirred with activated carbon at room temperature for 1 hour. The activated carbon was removed by filtration and the filtrate was concentrated and purified by column chromatography (activated alumina) to give a cyclic guanidine salt having the ion designated by chemical formula I as a cation and a bis(trifluoromethanesulfonyl)imide ion as an anion in the form of a light yellow oil.

1H-NMR (CDCl$_3$); δ 3.70 (s, 4H), 3.63 (t, J=6.58, 4H), 3.06 (s, 6H), 1.96 (t, J=6.58 Hz, 4H).

A 2M propylene carbonate solution of the cyclic guanidine salt obtained above was measured for the ionic conductivity by the AC impedance method and the results are shown in Table 1. A CV measurement made on the cyclic guanidine salt showed that the potential window was from −2.77 to 1.63 V against Ag/Ag+.

TABLE 1

| Temperature (° C.) | Ionic conductivity (mS/cm) |
|---|---|
| 40 | 13.4 |
| 30 | 10.5 |
| 20 | 8.1 |
| 10 | 6.0 |
| 0 | 4.3 |
| −10 | 2.9 |

Examples 2-5

Cyclic guanidine salts having a bis(trifluoromethanesulfonyl)imide ion as an anion were obtained as in Example 1 except substituting the compounds shown in Table 2 for pyrrolidine. The cyclic guanidine salts thus obtained were dissolved in propylene carbonate to a concentration of 2M and measured for the ionic conductivity by the AC impedance method at 20° C. on the one hand and they were analyzed by 1H-NMR (CDCl$_3$) on the other and the results are shown in Table 2. All of the cyclic guanidine salts obtained in Examples 1-5 are ionic liquids.

TABLE 2

| Ex. | Raw material | Property | Ionic conductivity (mS/cm) | 1H-NMR(CDCl3) |
|---|---|---|---|---|
| 2 | piperidine (H-N, 6-membered ring) | Yellow oil | 5.6 | δ 3.74 (s, 4H), 3.36 (brs, 4H), 3.00 (s, 6H,), 1.69 (brs, 6H,). |
| 3 | 2-methylpiperidine | Light yellow solid m.p. 40° C. | 5.2 | δ 4.01 (m, 2H), 3.78 (m, 1H), 3.54 (m, 2H), 3.41 (m, 1H), 3.27 (m, 1H), 2.99 (s, 6H), 1.67 (m, 6H), 1.33 (d, 3H) |
| 4 | morpholine | Light yellow solid m.p. 53° C. | 4.8 | δ 3.79 (t, J = 4.64 Hz, 4H), 3.78 (s, 4H), 3.45 (t, J = 4.64 Hz, 4H,), 3.03 (s, 6H). |
| 5 | thiazolidine | Yellow oil | 5.3 | δ 4.50 (s, 2H), 3.80 (s, 4H), 3.81 (t, J = 6.34 Hz, 2H), 3.13 (t, J = 6.34 Hz, 2H), 3.08 (s, 6H). |

Example 6

In 20 mL of dichloromethane was dissolved 2.03 g (10 millimoles) of the cyclic guanidine salt obtained in accordance with the procedure of Example 1. To this solution was added 0.89 g (10 millimoles) of sodium dicyanamide and stirred at room temperature for 12 hours. The white precipitate formed was removed by filtration and the filtrate was concentrated in a rotary evaporator. The residue was purified by column chromatography (activated alumina) to give a cyclic guanidine salt having the ion designated by chemical formula I as a cation and a dicyanamide ion as an anion. The cyclic guanidine salt thus obtained is an ionic liquid with a melting point of 62° C.

Examples 7-11

Cyclic guanidine salts were obtained according to the same procedure as in Example 6 with the exception of substituting the raw materials shown below for sodium dicyandiamide.

Example 7

Diformyl Sodium

Example 8

Sodium Thiocyanate

Example 9

Sodium Methyl Sulfate

Example 10

Sodium Dodecanesulfonate

Example 11

S-Sodium Ethanethiosulfonate

A 2M propylene carbonate solution of each of the cyclic guanidine salts obtained in Examples 6-11 was measured for the ionic conductivity at 20° and the results are shown in Table 3. All of the cyclic guanidine salts obtained in Examples 6-11 are ionic liquids.

TABLE 3

| Ex. | Property | Ionic conductivity (mS/cm) |
| --- | --- | --- |
| 6 | White solid m.p. 62° C. | 20.0 |
| 7 | Yellow oil | 7.6 |
| 8 | White solid m.p. 82° C. | 17.9 |
| 9 | Colorless oil | 13.0 |
| 10 | Colorless oil | 4.5 |
| 11 | Brown oil | 9.5 |

INDUSTRIAL APPLICABILITY

An electrochemical device such as a lithium ion primary battery, a lithium ion secondary battery, a dye-sensitized solar cell, an electric double layer capacitor, and an electrochromic device fabricated by the use of an electrolyte containing an ionic liquid comprising a cyclic guanidine salt of this invention exhibits excellent low-temperature properties and long-term stability.

The invention claimed is:

1. An ionic liquid comprising a cyclic guanidine salt represented by the following formula (1):

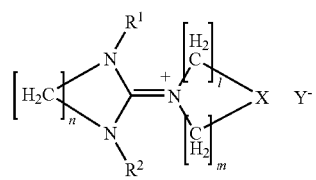

(1)

wherein $R^1$ and $R^2$ each is independently an alkyl group or an alkoxyalkyl group and X is a methylene group; $1+m=3$, and n is 2; and $Y^-$ is a monovalent anion.

2. The ionic liquid as described in claim 1 wherein $Y^-$ in formula (1) is an anion selected from the group of $(R^4SO_2)_2N^-$, $R^4SO_3^-$, $R^4COO^-$, $BF_4^-$, $PF_6^-$, $NO_3^-$, $(CN)_2N^-$, $(CHO)_2N^-$, $NCS^-$, $R^4OSO_3^-$, $R^4SO_2S^-$, and halogen ions and $R^4$ is a perfluoroalkyl group, an alkyl group, or an aromatic group.

3. A method for producing the ionic liquid described in claim 1 which comprises using a cyclic urea represented by formula (2) and a compound represented by formula (3) as raw materials and reacting them:

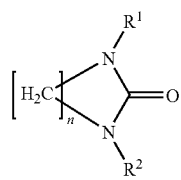

(2)

wherein, $R^1$ and $R^2$ each is independently an alkyl group or an alkoxyalkyl group, and n is 2;

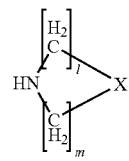

(3)

wherein, X is a methylene group, and $1+m=3$.

4. The method for producing the ionic liquid as described in claim 3 wherein a reaction accelerator is allowed to exist in the reaction of the cyclic urea represented by formula (2) with the compound represented by formula (3).

5. The method for producing the ionic liquid as described in claim 3 wherein the cyclic urea represented by formula (2) is first made to react with the reaction accelerator and then with the compound represented by formula (3).

6. An electrolyte comprising the ionic liquid described in claim 1.

7. An electrochemical cell using the electrolyte described in claim 6 as its electrolyte.

8. The ionic liquid as described in claim 1 wherein a cationic moiety of the cyclic guanidine salt represented by formula (1) is selected from a group consisting of the following formulas 1, 11 and 12

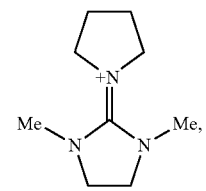

1

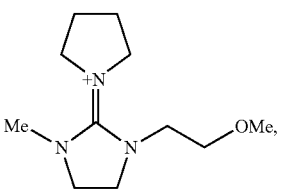

11

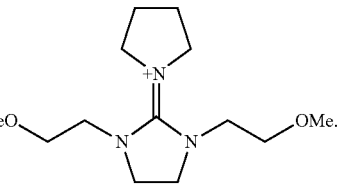

12

9. The ionic liquid as described in claim 1 wherein $R^1$ and $R^2$ each is independently a methyl group.

* * * * *